United States Patent [19]

Kurahashi et al.

[11] Patent Number: 4,591,562

[45] Date of Patent: May 27, 1986

[54] METHOD FOR PRODUCING L-PHENYLALANINE BY FERMENTATION

[75] Inventors: Osamu Kurahashi, Kawasaki; Takayasu Tsuchida, Yokohama; Hiroki Kawashima, Kawasaki; Hitoshi Enei, Zushi, all of Japan

[73] Assignee: Ajinomoto Company Incorporated, Tokyo, Japan

[21] Appl. No.: 519,714

[22] Filed: Aug. 2, 1983

[51] Int. Cl.4 .................. C12P 13/22; C12P 21/00; C12P 21/02; C12P 19/34; C12N 15/00; C12N 1/20; C12N 1/00; C12R 1/125; C07H 21/04

[52] U.S. Cl. ............................ 435/108; 435/68; 435/70; 435/91; 435/172.3; 435/253; 435/839; 435/317; 536/27; 935/29; 935/60; 935/74

[58] Field of Search .................. 435/108, 68, 70, 71, 435/91, 172.3, 253, 839, 317; 536/27; 935/29, 60, 74

[56] References Cited

U.S. PATENT DOCUMENTS 4,407,952 10/1983 Tsuchida et al. .................. 935/60

FOREIGN PATENT DOCUMENTS 2053906 11/1981 United Kingdom .................. 935/60

OTHER PUBLICATIONS

Williams et al: in *Molecular Cloning and Gene Regulation in Bacilli*, Ganesan et al (Ed.), Academic Press, New York, 1982, pp. 91–95.

Yoneda: in *Molecular Cloning and Gene Regulation in Bacilli*, Ganesan et al (Ed.), Academic Press, New York, 1982, pp. 111–120.

Kreft et al: in *Molecular Cloning and Gene Regulation in Bacilli*, Ganesan et al (Ed.), Academic Press, New York, 1982, pp. 145–157.

*Primary Examiner*—Thomas G. Wiseman
*Assistant Examiner*—James Martinell
*Attorney, Agent, or Firm*—Oblon, Fisher, Spivak, McClelland & Maier

[57] ABSTRACT

A method for producing L-phenylalanine by fermentation which comprises aerobically culturing an L-phenylalanine-producing microorganism in an aqueous culture medium and recovering the L-phenylalanine accumulated in the culture medium, the L-phenylalanine-producing microorganism having been constructed by incorporating a recombinant plasmid DNA, into which a DNA fragment controlling resistance to a phenylalanine antagoinst, obtained from a chromosomal DNA of a mutant of the genus Bacillus resistant to the phenylalanine antagonist, has been inserted, into a recipient strain of the genus Bacillus.

4 Claims, No Drawings

METHOD FOR PRODUCING L-PHENYLALANINE BY FERMENTATION

BACKGROUND OF THE INVENTION

1. Field of the Invention

The present invention relates to a method for producing L-phenylalanine by fermentation, and particularly to a method for producing L-phenylalanine with a microorganism of the genus Bacillus constructed by a gene splicing technique.

2. Description of the Prior Art

In the past, in order to render a wild strain capable of producing L-phenylalanine by fermentation, it has been necessary to induce artificial mutants from the wild strain. In this regard, there are many known L-phenylalanine producing artificial mutants.

Examples of known phenylalanine producing microorganisms include mutants of Bacillus subtilis (J. Biol. Chem., 242, 4948 (1967), mutants of Corynebacterium or Brevibacterium resistant to phenylalanine-analogue (U.S. Pat. No. 3,660,235), mutants of Corynebacterium resistant to phenylalanine-analogue and requiring L-tyrosine for growth, and mutant of Brevibacterium resistant to phenylalanine-analogue and tryptophan-analogue and requiring L-tyrosine for growth (U.S. Pat. No. 3,909,353).

Another approach to increase the productivity of phenylalanine in microorganisms is suggested as to Escherichia in Japanese Published Unexamined Patent Application No. 165798/1979), in which *Escherichia coli* strains transformed with a recombinant plasmid DNA and constructed by a gene splicing technique to produce L-phenylalanine are disclosed.

However, it is desirable still to produce L-phenylalanine by fermentation in higher efficiency than the known methods.

SUMMARY OF THE INVENTION

It has now been found that the L-phenylalanine-producing microorganisms, which have been constructed by introducing a recombinant plasmid, DNA into which a chromosomal DNA fragment controlling resistance to a phenylalanine-antagonist obtained from a mutant of the genus Bacillis resistant to the phenylalanine antagonist has been inserted, into a recipient strain of the genus Bacillus, produce L-phenylalanine in higher yield than the mutant used as the DNA-donor or the recipient strain.

DETAILED DESCRIPTION OF PREFERRED EMBODIMENTS

The L-phenylalanine-producing microorganisms used in the method of the present invention are constructed by introducing a recombinant plasmid DNA into which a chromosomal DNA fragment controlling resistance to a phenylalanine-antagonist obtained from a mutant of the genus Bacillus resistant to the phenylalanine-antagonist has been inserted, into a recipient strain of the genus Bacillus.

The phenylalanine-antagonists of the present invention inhibit the growth of Bacillus, but the inhibition is suppressed partly or completely when L-phenylalanine coexists in the medium. Examples of the phenylalanine-antagonists are o, m or p-fluorophenylalanine, o, m or p-aminophenylalanine, β-phenylserine, cyclohexylserine, α-amino-β-phenylethanesulfonic acid, o, m or p-bromophenylalanine, β-2-thienylalanine, β-3-thienylalanine, 1-cyclo-phenthene-1-alanine, 1-cyclohexene-1-alanine, 2-amino-4-methyl-hexenic acid, S-(1, 2-dichlorovinyl)-cysteine, β-4-pyridylalanine, β-2-pyridylalanine, β-4-pyrazolealanine and p-nitrophenylalanine.

Although any mutants of the genus Bacillus resistant to phenylalanine-antagonist can be used as the DNA-donors for chromosomal DNA fragment controlling resistance to the phenylalanine-antagonist, mutants having high resistance to the phenylalanine-antagonist are preferred. In many cases, better results can be obtained when a mutant having high productivity of L-phenylalanine is used as the DNA-donor. The mutant resistant to the phenylalanine-antagonist can be obtained in a conventional manner such as exposing the parent strain to 250 μg/ml of N-methyl-N'-nitro-N-nitrosoguanidine, and isolating the strain capable of growing in a medium containing an amount of the phenylalanine-antagonist inhibitive to the growth of the parent strain.

Extraction of chromosomal DNA can be carried out in a conventional manner as described in Bacteriol, 89, 1065, (1965).

As the vector DNA, plasmid DNAs which propagate in hosts of Bacillus are used. Typical vector DNAs are pCT 127, pC 194, pC 221, pC 223 and pUB 112 (Proc. Natl, Acad, Sci. U.S.A., 74, 1680–1682 (1977)), pUB 110 (J. Bacteriol., 134, 318–329 (1978), and pTP 4 and pTP 5 (Microbiol Letters, 5, 55–59 (1978)), all of which are derived from plasmids of Staphylococcus, and pLS 15 and pLS 28 (J. Bacteriol., 131, 699–701 (1977)), pLS 13 (J. Bacteriol., 129, 1487–1494 (1977)), and pPL, pPL 2 (J. Bacteriol 124, 484 (1975), all of which are derived from plasmids of Bacillus.

The chromosomal DNA is digested with a restriction endonuclease by a well known method (Biochem. Biophys. Acta, 383, 457, (1975)). Various kinds of restriction endonucleases can be used if the degree of digestion is controlled by changing reaction time.

The vector DNA is also cleaved with a restriction endonuclease. Suitable restriction endonuclease for each vector DNA is disclosed in the literature shown in the parenthesis above.

Recombination of DNA to prepare the recombinant plasmid can be carried out by the ligation reaction with a ligase, or by incorporating with terminal transferase deoxyadenylic acid and thymidylic acid, or deoxyguanylic acid and deoxycytidylic acid into the chromosomal DNA fragment and cleaved vector DNA and by subjecting the modified chromosomal DNA fragment and cleaved DNA to an annealing reaction.

The recombinant DNA thus obtained can be incorporated into the DNA-recipient by treating the cell of the DNA-recipient with calcium chloride to increase permeability as is reported regarding *E. coli* K-12 (Mandel, M. and Higa, A., J. Mol. Biol., 53, 159 (1970)), or by applying for the incorporation cells of the DNA-recipient at a specific stage of growth when cells become capable of incorporating plasmids (competent cell) as is reported in *Bacillus subtilis* (Duncan, C. H., Wilson, G. A. and Young, F. E., Gene 1, 153 (1977)). The recombinant DNA can also be incorporated into the DNA-recipient by forming a protoplast or spheroplast of the DNA-recipient which easily incorporates plasmid DNA as is known in *Bacillus subtilis*, actinomycetes and yeast (Chang, S. and Cohen, S. N., Molec, Gen. Genet, 168, 111 (1979); Bibb, M. J. Ward, J. M. and Hopwood, O. A., Nature, 274, 398 (1978); Hinnen, A., Hicks, J. B. and Fink, G. R., Proc. Natl, Acad. Sci., USA, 75, 1929 (1978)).

The recipients for the recombinant DNA are microorganisms of the genus Bacillus. It is convenient to use, as the DNA recipient, microorganisms sensitive to a phenylalanine-analogue and requiring phenylalanine for growth for the selection of transformant having a recombinant DNA inserted with chromosomal DNA fragment controlling resistance to phenylalanine-antagonist. When the recombinant plasmid DNA into which a chromosomal DNA fragment controlling resistance to a phenylalanine-antagonist has been inserted is used for transformation after selection of the recombinant plasmid DNA using a host sensitive to phenylalanine-antagonist and requiring L-phenylalanine for growth, microorganisms resistant to phenylalanine-antagonist and having no requirement of L-phenylalanine for growth can be used as the DNA recipient.

The desired transformants are those which become resistant to phenylalanine-antagonist and are capable of producing L-phenylalanine when microorganisms sensitive to phenylalanine-antagonist and requiring L-phenylalanine for growth are used as the recipients. When microorganisms resistant to phenylalanine-antagonist and having no requirement of L-phenylalanine for growth, the desired transformants are those which have the characteristics possessed by the vector DNA as the marker for selection.

The methods of cultivation of the L-phenylanine producing transformants thus obtained are conventional, and are similar to the methods for the cultivation of known L-phenylanine producing microorganisms. The aqueous culture medium employed is a conventional one containing a carbon source, nitrogen source, inorganic ions and, when required, minor organic nutrients such as vitamine and amino acids.

As to the carbon source, carbohydrate such as glucose, sucrose, lactose, fructose and raw material containing such saccharides (such as starch hydrolysate, molasses and fruit juice) is used. Gaseous ammonia, aqueous ammonia, ammonium salts and other nitrogen containing materials can be used as the nitrogen source.

Cultivation is conducted under an aerobic condition in which the pH and the temperature of the aqueous culture medium are adjusted to a suitable level previously determined and continued until production of L-phenylalanine ceases.

EXAMPLE 1

(1) Extraction of chromosomal DNA

Bacillus subtilis AJ 11773 (FERM-P 6319=FERM-BP 237) requiring L-arginine and L-leucine and resistant to DL-m-fluorophenylalanine was cultured in 1 l of "Bact Penassay Broth" (Difco) at 30° C. for 2 hours with shaking, and cells in exponential growth phase were harvested. Chromosomal DNA was extracted from the cells by a conventional phenol-method, (J. Bacteriol., 89, 1065 (1965), and 3.8 mg of purified DNA was obtained.

(2) Insertion of chromosomal DNA fragment into vector

As the vector, pUB 110 possessing genetic information of kanamycin-resistance and neomycin-resistance was used.

Ten $\mu$g of the chromosomal DNA obtained in step (1) and 5 $\mu$g of the vector DNA were digested separately with endonuclease Eco RI at 37° C. for 1 hour, and thereafter the two reaction mixture were heated at 65° C. for 10 minutes and mixed. The mixed solution was subjected to ligation reaction by a $T_4$ phage DNA-ligase in the presence of ATP and dithreitol at 10° C. for 24 hours.

(3) Genetic transformation with the plasmid having phenylalanine producing gene.

Bacillus subtilis AJ 11772 (FERM-P 6318=FERM-BP 236) which requires L-arginine, L-leucine and L-phenylalanine was cultured in "Penassay Broth" (Difco) at 30° C. overnight with shaking, and thereafter cultured at 37° C. for 4 hours with shaking in Medium-I (containing 0.5 g/dl glucose, 0.2 g/dl $(NH_4)_2SO_4$, 0.6 g/dl $KH_2PO_4$, 1.4 g/dl $K_2HPO_4$, 0.02 g/dl $MgSO_4.7H_2O$, 0.1 g/dl sodium citrate, 0.2 g/dl yeast extract, 5 mg/dl L-phenylalanine, 25 mg/dl L-arginine and 5 mg/dl L-leucine), and further cultured, after the cultivation in Medium-I, at 37° C. for 1.5 hours with shaking in Medium-II (containing 0.5 g/dl glucose, 0.2 g/dl $(NH_4)_2SO_4$, 0.6 g/dl $KH_2PO_4$, 1.4 g/dl $K_2HPO_4$, 0.12 g/dl $MgSO_4.7H_2O$, 0.1 g/dl sodium citrate, 0.02 g/dl yeast extract, 5 mg/dl L-arginine and 0.5 mg/dl L-leucine). Thus, competent cells having the ability of plasmid uptake were obtained. (C. Anagnostopoulos, J. Spizizen: J. Bacteriol., 81, 741, (1961)).

The suspension of the competent cells was added the recombinant plasmid obtained in step (2), and the mixture was incubated at 37° C. for 2 hours with shaking to complete the transformation reaction.

The cell-suspension was transferred onto a minimum medium prepared by adding 5 $\mu$g/dl kanamycin, 10 mg/dl L-leucine, 10 mg/dl L-leucine, 10 mg/dl L-arginine, 100 mg/dl D, L-m-fluorophenylalanine and 2 g/dl agar to a basal minimum medium of pH 7.2 containing 0.6 g/dl $KH_2PO_4$, 1.4 g/dl $K_2HPO_4$, 0.2 g/dl $(NH_4)_2SO_4$, 0.1 g/dl sodium citrate, 0.02 g/dl $MgSO_4.7H_2O$, and 0.5 g/dl glucose. After 3 days cultivation at 37° C., two colonies appeared on the agar-medium.

Among the transformants, AJ 11774 (FERM-P 6320=FERM-BP 238) which had highest productivity of L-phenylalanine was selected. DNAs in AJ 11774 was extracted by C. I. Kado's phenol method (J. Bac., 145, 3, 1365 (1981)). Plasmid DNA and chromosomal DNA were separated by agarose-gel electrophoresis, and plasmid DNA obtained was purified by dialysis.

The purified plasmid DNA was incorporated into AJ 11773, which produces L-phenylalanine, by the manner shown in step (3), and as the desired transformant, kanamycin-resistant AJ 11775 (FERM-P 6321=FERM-BP 239) was obtained.

(4) Phenylalanine production by the new phenylalanine producers

L-phenylalanine productivity of AJ 11773, AJ 11774 and AJ 11775 was tested as follows.

Twenty ml batches of a culture medium at pH 7.0, which contained, per deciliter, 8 g glucose, 1 g $NH_4Cl$, 0.2 g KCl, 0.1 g $KH_2PO_4$, 0.04 g $MgSO_4.7H_2O$, 0.4 g "casamino acid" (Difco), 1 mg $FeSO_4.4H_2O$, 1 mg $MnSO_4.4H_2O$, 20 mg L-arginine, 20 mg L-leucine and 4 g $CaCO_3$, were placed in 500-ml shaking flasks. Five $\mu$g/ml kanamycin was added further to the medium for AJ 11774 and AJ 11775.

Cultivation was carried out at 30° C. for 96 hours with shaking.

The amounts of L-phenylalanine in the supernatant of the resulting culture media were determined, and are shown in Table 1.

TABLE 1

| Microogranism tested | L-phenylalanine accumulated (mg/d) |
|---|---|
| AJ 11773 | 162 |
| AJ 11774 | 185 |
| AJ 11775 | 288 |

*Bacillus subtilis* AJ 11772, *Bacillus subtilis* AJ 11773, *Bacillus subtillis* AJ 11774 and *Bacillus subtillis* AJ 11775 have the taxonomic characteristics as disclosed in Proc. Sec. Int. Congr. Microbiol. (London, 1936) 245 (1937) and Nomencl. Comm. Intern. Soc. Microbiol., 28, (1937), and in addition have characteristics as disclosed hereinabove.

*Bacillus subtilis* AJ 11772, AJ 11773, AJ 11774 and AJ 11775 were deposited at the Fermentation Research Institute, Japan, on the Jan. 27, 1982 under the accession numbers FERM-P 6318, FERM-P 6319, FERM-P 6320 and FERM-P 6321, respectively, which deposits were converted to deposits under the Budapest Treaty in January, 1983.

What is claimed is:

1. A method for producing L-phenylalanine by fermentation which comprises aerobically culturing an L-phenylalanine-producing microorganism in an aqueous culture medium, and recovering the L-phenylalanine accumulated in the culture medium; said L-phenylalanine producing microorganism having been constructed by incorporating a recombinant plasmid DNA, into which a DNA fragment controlling resistance to a phenylalanine-antagonist, obtained from a chromosomal DNA of a mutant of the species *Bacillus subtilis* resistant to the phenaylalanine-antagonist, has been inserted, into a recipient strain of the species *Bacillus subtilis*.

2. The method of claim 1, wherein said phenylalanine-antagonist is m-fluorophenylalanine.

3. The method of claim 1, wherein said recipient strain requires L-phenylalanine for growth.

4. The method of claim 1, wherein said recipient strain is resistant to a phenylalanine-antagonist.

* * * * *